United States Patent

Wilk

Patent Number: 5,322,521
Date of Patent: Jun. 21, 1994

[54] PLUME EVACUATION METHOD

[76] Inventor: Peter J. Wilk, 185 W. End Ave., New York, N.Y. 10023

[21] Appl. No.: 937,599

[22] Filed: Aug. 31, 1992

Related U.S. Application Data

[63] Continuation-in-part of Ser. No. 530,214, May 30, 1990, Pat. No. 5,211,639, and a continuation-in-part of Ser. No. 839,301, Feb. 20, 1992, Pat. No. 5,279,599.

[51] Int. Cl.$^5$ .............................................. A61M 1/00
[52] U.S. Cl. ...................................... 604/317; 604/49; 604/53; 604/281; 433/91
[58] Field of Search ........................ 433/91, 93, 94, 96; 604/95, 49, 53, 275, 281, 284, 315, 317, 319, 321, 322; 261/118

[56] References Cited

U.S. PATENT DOCUMENTS

| | | |
|---|---|---|
| 2,814,529 | 11/1957 | Arnt . |
| 2,972,346 | 2/1961 | Eddings . |
| 3,091,859 | 6/1963 | Baughan ............................ 433/96 |
| 3,403,677 | 10/1968 | Struve . |
| 3,625,207 | 12/1971 | Agnew . |
| 4,419,301 | 12/1983 | Nahra ................................ 261/118 |
| 4,568,338 | 2/1986 | Todd . |
| 4,692,153 | 9/1987 | Berlin et al. . |
| 4,790,809 | 12/1988 | Kuntz . |
| 4,790,810 | 12/1988 | Pugh, Jr. et al. . |
| 4,820,262 | 4/1989 | Finney . |
| 4,921,492 | 5/1990 | Schultz et al. ..................... 604/317 |
| 4,925,452 | 5/1990 | Melinyshyn et al. . |
| 4,935,004 | 6/1990 | Cruz . |
| 5,015,243 | 5/1991 | Schifano . |
| 5,127,411 | 7/1992 | Schoolman et al. ................. 433/91 |
| 5,215,539 | 6/1993 | Schoolman .......................... 604/317 |

Primary Examiner—Randall L. Green
Assistant Examiner—Rob Clark
Attorney, Agent, or Firm—R. Neil Sudol; Henry D. Coleman

[57] ABSTRACT

A method for use during laser surgery comprises the steps of providing a flexible hose having a plurality of apertures spaced from each other along a distal end portion of the hose and forming a portion of the hose into an arcuate segment about an opening in a patient. A distal end segment of the hose is inserted through the opening into a body cavity of the patient. A proximal end of the hose is connected to a suction source, and suction is applied to the hose to draw in air through apertures in the arcuate segment and in the distal end segment.

12 Claims, 3 Drawing Sheets

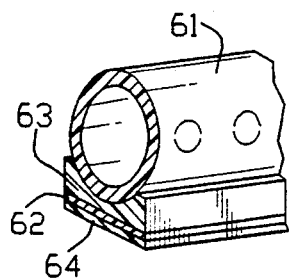
FIG. 5
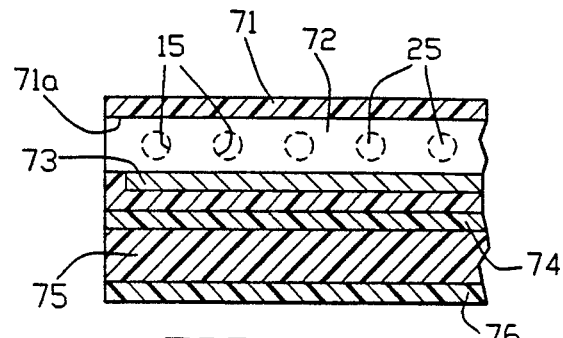
FIG. 6
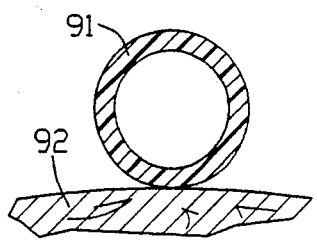
FIG. 8
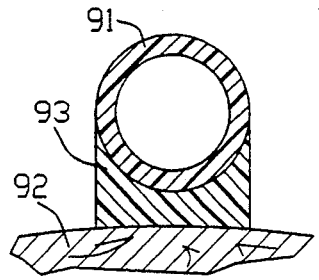
FIG. 9
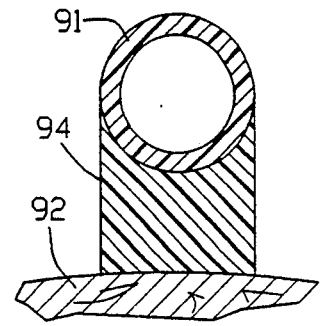
FIG. 10
FIG. 11

PLUME EVACUATION METHOD

CROSS-REFERENCE TO RELATED APPLICATION

This application is a continuation-in-part of commonly owned U.S. patent application Ser. No. 530,214 filed May 30, 1990 now U.S. Pat. No. 5,211,639 and of U.S. patent application Ser. No. 839,301 filed Feb. 20, 1992 now U.S. Pat. No. 5,279,599.

BACKGROUND OF THE INVENTION

This invention relates to a method for drawing off gases and particulate matter from a burning site. More particularly, this invention relates to a method for drawing off gases and particulate matter from a surgical site, especially during the performance of laser surgery.

Lasers are employed in dermatological surgery to remove such skin conditions as warts and cancerous tissues. A laser burns off the unwanted tissues and in so doing generates an odiferous by-product known as a "plume." The plume includes gases and particulate matter and may further include bacteria and viruses such as the AIDS virus. Accordingly, it is important to evacuate the plume from the surgical environs as effectively as possible.

A plume evacuator currently on the market comprises a rigid hollow ring provided on an inwardly facing surface with a series of holes. The ring is connected to a vacuum generator and placed around the surgical site. During the laser operation, the vacuum generator or pump draws off the plume through the holes in the ring. The vacuum unit includes a filter which filters out the particulate matter. The filtered air is then returned to the operating room.

A disadvantage with that plume evacuator is that the fixed nature of the ring is not adaptable to the particular surgical conditions. For example, the ring is of a fixed diameter and cannot be adapted to differently sized surgical sites. This reduces the efficiency of the evacuator and may in some circumstances allow a portion of the plume to escape into the ambient atmosphere.

OBJECTS OF THE INVENTION

An object of the present invention is to provide a plume evacuation technique.

A more particular object of the present invention is to provide a plume evacuation method for use in laser surgery within natural orifices such as the mouth, the vagina, and the rectum and within incisions.

A further specific object of the present invention is to provide such a plume evacuation method which is at least partially adaptable to a surface about a surgical site.

An additional object of the present invention is to provide a plume evacuation method which can be located at a varying distance from a surgical site.

SUMMARY OF THE INVENTION

A method for use during laser surgery comprises, in accordance with the present invention, the steps of (a) providing a flexible hose having a plurality of apertures spaced from each other along a distal end portion of the hose, (b) forming a portion of the hose into an arcuate segment about an opening in a patient, (c) inserting a distal end segment of the hose through the opening into a body cavity of the patient, (d) connecting a proximal end of the hose to a suction source, and (e) applying suction to the hose to draw in air through apertures in the arcuate segment and in the distal end segment.

Pursuant to another feature of the present invention, where the hose is provided with a form retention element attached to the hose for maintaining at least a portion of the hose in a selected substantially loop-shaped configuration, the method further comprises the step of using the form retention element to maintain the arcuate segment in an arcuate configuration.

Where the form retention element particularly includes a bendable memory strip, the method includes the step of bending the memory strip into a desired shape.

Where the form retention element particularly includes an adhesive strip extending along a length of the hose, the method also includes the step of pressing the adhesive strip to a skin surface about the opening.

The opening may be a natural body opening, such as the mouth, the anus or the vagina. Alternatively, the technique may be used to evacuate smoke during laser surgery performed through an incision in the patient.

Pursuant to another feature of the present invention, the hose is provided with covers attached to the hose for removably covering at least some of the suction apertures. In that event, the method further comprises the step of selectively removing the covers to expose apertures along the arcuate segment and the distal end segment prior to the application of suction.

Pursuant to another feature of the present invention, the hose may be bifurcated along the end segment into two hose sections each provided with a plurality of spaced apertures. One of the hose sections is formed into the arcuate segment, while the other section is inserted through the opening into the patient.

The present invention provides an improved plume evacuation method which is easily adaptable to different surgical conditions and specifically to differently sized body openings and to differently dimensioned body cavities. More specifically, the part of the evacuator hose arced about the opening may be shaped to conform to the opening, both in size and shape. The portion of the hose inserted into the body cavity may have a length adapted to the depth of the cavity and may, in addition, be shaped to conform to the internal configuration and size of the cavity in which the surgical site is located.

The use of a bendable metal strip and/or a releasable attachment component (e.g., adhesive strip), either individually or in combination with one another, allows the hose to assume the contour of the patient's body in a region about the surgical site.

The selectably openable apertures in a plume evacuation method in accordance with the present invention enable a surgeon or surgical assistant to optimize the locations of suction along the hose. Essentially, only apertures in an arcuate segment looped about an opening in the patient and in a segment inserted into the patient will be opened. Apertures in the hose which are too far from the surgical site, after the hose has been properly configured and disposed about the surgical site, remain closed, thereby maximizing suction through the apertures closest to the source of the plume.

Furthermore, a plume evacuation method in accordance with the present invention enables location of the hose at a varying distance from a surgical site. More specifically, the hose may be attached to a foam strip which is provided with an adhesive surface for attachment to the patient's body in a region about the surgical site. The foam strip or other pad distances the evacuation method hose from the skin surface and thereby enables an optimizing of the location of the suction apertures relative to the surgical site.

BRIEF DESCRIPTION OF THE DRAWING

FIG. 5 is a partial cross-sectional side view of an additional embodiment of an evacuator hose in accordance with the present invention.

FIG. 6 is a partial cross-sectional side view of a further embodiment of an evacuator hose in accordance with the present invention.

FIG. 8 is a diagrammatic end view of a plume evacuator hose in accordance with the present invention, showing that hose in relation to a skin surface.

FIG. 9 is a diagrammatic end view of the plume evacuator hose of FIG. 8, showing that hose in another relation to the skin surface.

FIG. 10 is a diagrammatic end view of the plume evacuator hose of FIG. 8, showing that hose in yet another relation to the skin surface.

FIG. 11 is a top view of another plume evacuator hose in accordance with the present invention.

DETAILED DESCRIPTION

Figure 1:
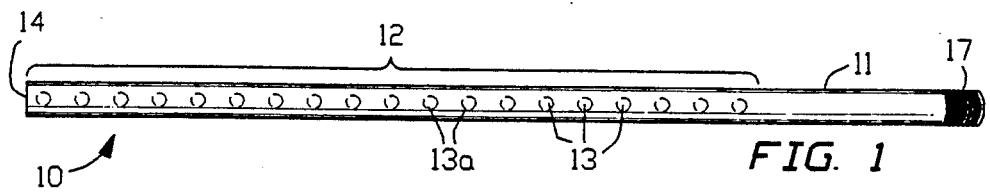
FIG. 1 is an elevational side view of a plume evacuator hose for use in a surgical method in accordance with the present invention.

As illustrated in FIG. 1, a plume evacuator device 10 comprises a flexible hose 11 provided along an end segment 12 with a plurality of equispaced equal-sized apertures 13 each stopped by a respective punch-out cover 13a formed from the sidewall of hose 11. At a free tip 14 of end segment 12, hose 11 may be open. At an end opposite tip 14, hose 11 is provided with a fastener part 17 for connecting the hose to a suction source or vacuum generator 18 (FIG. 4).

Figure 2:
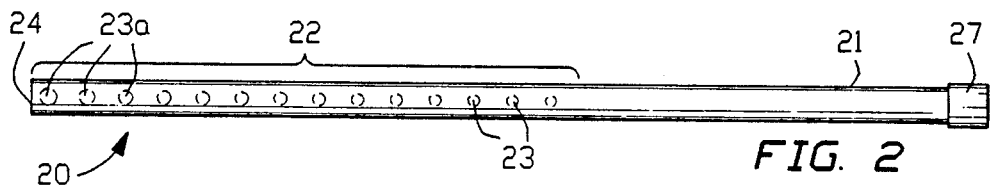
FIG. 2 is an elevational side view of another plume evacuator hose for use in a surgical method in accordance with the present invention.

Another plume evacuator device 20 is illustrated in FIG. 2. Device 20 similarly takes the form of a flexible hose 21, preferably made of synthetic resin material such as polyethylene, polypropylene, nylon or polytetrafluoroethylene. Hose 21 is provided along an end segment 22 with a linear array of substantially equispaced circular apertures 23 having diameters which decrease in a monotonic sequence from a free hose tip 24 towards an end of hose 21 which is provided with a coupling member 27 for connecting that hose end to suction source or vacuum generator 18 (FIG. 4). Apertures 23 are covered by respective punch-outs 23a formed in the sidewall of hose 21.

Figure 3:
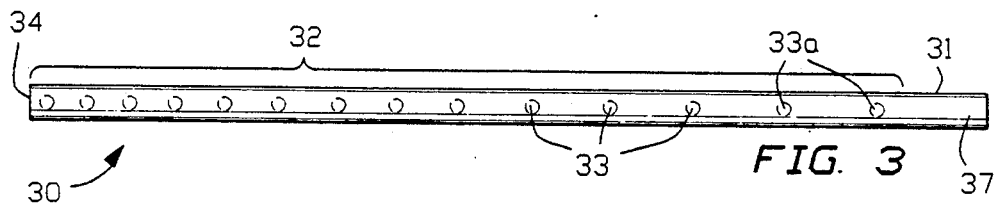
FIG. 3 is an elevational side view of yet another plume evacuator hose for use in a surgical method in accordance with the present invention.

Yet another plume evacuator assembly 30 is depicted in FIG. 3. Again, that plume evactuator assembly comprises a flexible synthetic resin hose 31 provided along an end segment 32 with a linear array of circular apertures 33 stopped by respective punch-out covers 33a formed from the sidewall of hose 31. Apertures 33 or punch-out perforations 33a have essentially the same diameter but are spaced at distances from each other which increase in a monotonic manner from a free hose tip 34 towards an end 37 of hose 31 which is connectable to suction source of vacuum generator 18 (FIG. 4). Hose end 37 is sufficiently resilient, for example, to receive a male inlet member (not illustrated) of suction source or vacuum generator 18 in an air-tight friction fit. At free tip or end 34, hose 31 may be opened or closed.

Figure 4:
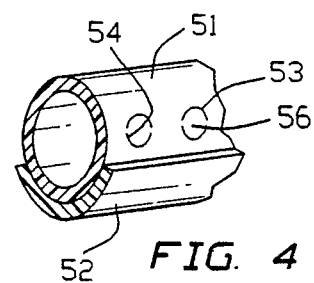
FIG. 4 is a partial cross-sectional side view of another embodiment of an evacuator hose for use in a method in accordance with the present invention.

As illustrated in FIG. 4, a plume evacuator hose 51, which may take the form of hose 11, 21, or 31, is provided along a longitudinally extending surface with an adhesive strip 52 for releasably attaching the evacuator hose to a patient's skin about a surgical site. Adhesive strip 52 serves to fix the hose at the surgical site so that it does not shift during the surgical procedure. In addition, the adhesive strip serves to conform hose 51 to the shapes of the patient's body in a region about the surgical site.

In its sidewall, hose 51 is provided with a plurality of circular score lines 53 which define a plurality of spaced apertures 54 which are closed by respective covers 56 integral with the hose sidewall. Selected covers 56 may be pressed inwardly into hose 51, thereby shearing those covers from hose 51 and opening the respective apertures 54. This punching out of the aperture covers 56, as well as aperture covers of any other hose embodiment disclosed herein, is undertaken after the respective hose, e.g., hose 51, has been configured to conform to a surgical site. The removal of selected covers 13a, 23a, 33a, 56, etc., to open the apertures 13, 23, 33, 54, etc., closest to the surgical site may be undertaken while the respective hose, 11, 21, 31, 51 is located on the patient. Alternatively, the hose may be temporarily removed from the patient, the holes punched and the hose replaced in the original position and configuration.

As depicted in FIG. 5, a plume evacuator hose 61, which may take the form of hose 11, 21, or 31, is provided along a longitudinally extending surface with an adhesive strip 62 attached to the hose via a buffer strip or cushion 63. Cushion 63 is made of a resilient foam-like material and serves to maximize the surface of the adhesive strip 62 which is in contact with the patient's skin surface at the surgical site. Adhesive strip 62 is preferably a two-sided adhesive strip and is covered, during shipping and prior to use of the plume evacuator, with a release liner 64.

As illustrated in FIG. 6, another plume evacuator hose 71 in accordance with the present invention is provided on an inner surface 72 with memory strip 73 in the form of an elongate metallic member. A two-sided adhesive strip 74 joins to an outer surface of hose 71 an elongate spacer member 75 which serves to set hose 71 at a distance from a surgical site, in a direction measured generally perpendicularly to the surface of the site. Spacer member 75 is provided along a side opposite tube or hose 71 with an adhesive layer 76 for attaching the hose to the patient's skin about the site of the surgery. A free end of hose 71 may have an opening 71a. Opening 71a may be covered with a removable tape strip (not shown) or a punch-out (not shown) whereby the free end may be selectively opened to air flow in response to an application of suction during a surgical operation.

It is to be noted that memory strip 73 may be embedded in the wall of hose 71 or may, alternatively, be fastened to the outside of the hose. As discussed hereinabove with respect to FIGS. 1–4, hose 71 is provided along its length with a series of spaced apertures 15 with removable covers 25 (e.g., tape strips or punch-outs).

Figure 7:
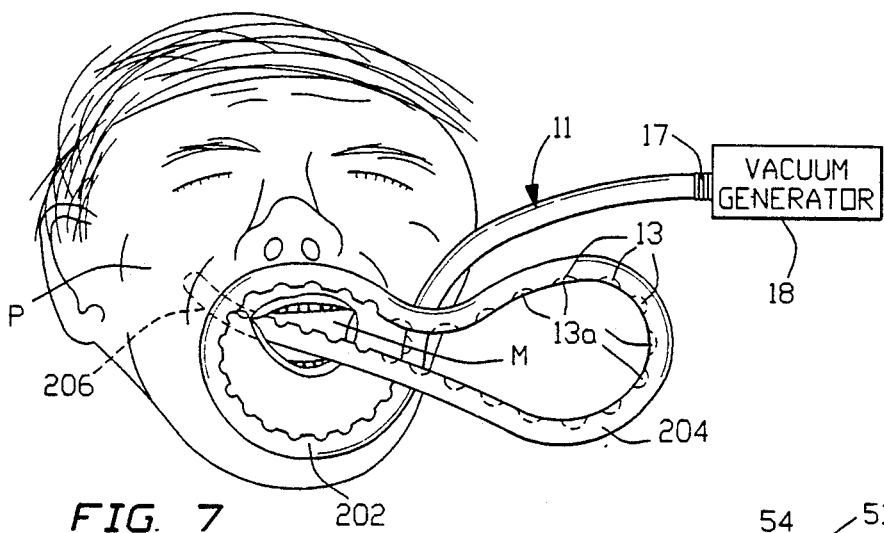
FIG. 7 is a diagrammatic perspective view of the plume evacuator hose of FIG. 1, showing the evacuator hose connected to a vacuum generator and in use during a surgical operation in accordance with the present invention.

A specific use of a plume evacuator device 10, 20, or 30 in conjunction with laser surgery in the mouth M of a patient P is depicted in FIG. 7, with reference particularly to device 10 of FIG. 1. In implementing the method illustrated in FIG. 7, hose 11 is provided along at least a portion of its length with a shape retention component (not illustrated in FIGS. 1 or 7) in the form, for instance, of an adhesive strip such as strip 52 or 62 (FIGS. 4, 5) or a bendable memory strip such as metallic member 73 (FIG. 6). A central segment 202 of hose 11 is bent about mouth M of patient P and maintained in a substantially circular or loop shaped configuration by the shape retention component. Preferably, hose 11 is configured so that apertures 13 are facing inwardly, towards mouth M. However, the apertures 13 may also be pointed in an upward direction. Covers or punch-outs 13a of apertures 13 along segment 202 are removed. A more distally located middle segment 204 is looped upwardly away from patient P so that a distal end segment 206 may be inserted into the patient's mouth M. Prior to a final disposition of distal end segment 206 inside mouth M, covers or punch-outs 13a of apertures 13 along segment 206 are removed. In the event that the distal tip of hose 11 has a transversely extending wall with a covered opening (not shown), the opening cover may be removed prior to the final disposition of distal end segment 206 in anticipation of laser surgery. The removal of a distal tip cover is determined in part by the location of the surgial site within the mouth M. In addition, several apertures 13 may be opened along a portion of hose 11 immediately outside mouth M.

Although a shape retention component in the form of memory strip or metallic member 73 is perhaps more effective in controlling the shape of middle segment 204, that hose segment may also be maintained in an upwardly and/or outwardly projecting loop configuration by adhesive forces exerted on central segment 202 and a force fit of distal end segment 206 inside mouth M by virtue of inherent spring bias of hose 11.

Adhesive strip 52 (FIG. 5) or 62 (FIG. 6) may be severed at the proximal end of distal end segment 206. The severed distal end portion of strip 52 or 62 may then be removed from distal end segment 206 prior to final disposition of that segment inside mouth M.

With further reference to FIG. 7, the fastener part or coupling member 17, 27 or 37 is connected to suction source or vacuum generator 18. This connection may be implemented before or after the configuration of hose 11 as illustrated in FIG. 7.

During a cauterization or burning operation performed by a surgeon using a laser instrument (not shown), smoke resulting from the burning of the skin tissues by a laser beam is sucked through apertures 13, 23 or 33 which are opened prior to the commencement of the laser operation by pushing out the respective punch-out covers 13a, 23a, 33a. The smoke is then sucked along the length of the respective hose 11, 21 or 31 to vacuum generator 18 where the air is filtered of particulate material and possible gaseous substances and returned to the air of the operating room or, alternatively, to a disposal conduit.

The configuration of hose 11 shown in FIG. 7 and the associated method for use in laser surgery may be applied to other openings and cavities other than the mouth. For example, the same technique may be used in disposing a plume suction hose at a natural body opening such as the anus or the vaginal orifice in preparation for surgery on the rectum or the sigmoidal colon or the vagina. The same technique may also be applied to laser surgery where an incision has been formed in a skin surface to provide laser access to an internal organ or tissue surface of the patient.

FIGS. 8, 9 and 10 diagrammatically illustrate three different relationships between a hose segment 91 and a skin surface 92. In FIG. 8, hose segment 91 is in direct contact with the skin surface. In FIG. 9, hose segment 91 is elevated above skin surface 92 by virtue of a spacer member 93. In FIG. 10, hose segment 91 is spaced a greater distance from skin surface 92 by interposition of a wider spacer member 94. Each tube or hose 91 may be sold with a plurality of spacer members 93 and 94, the surgeon or surgical assistant selecting the appropriate spacer member for the particular surgery to be performed.

As indicated in FIGS. 9 and 10, hose segment 91 may be disposed on spacer member 93 or 94 so that suction apertures 81 in the sidewall of the tube or hose segment may be angled towards a surgical site and more particularly towards an opening such as mouth M (FIG. 7) through which laser surgery is taking place.

As illustrated in FIG. 11, a plume evacuator hose 100 has a pair of flexible hollow prong sections 102 and 104 joined to one another at one end of a connector section 106 of hose 100. Connector section 106 is provided at an end opposite prong sections 102 and 104 with a coupling feature 108.

Prong sections 102 and 104 are provided along facing surfaces with a plurality of longitudinally spaced apertures 110 and 112 which are covered by respective punch-outs 110a and 112a formed in the sidewalls of prong sections 102 and 104. Each prong section 102 and 104 is further provided with a respective bendable metal strip or rod 114 and 116 attached along an internal surface of the prong section, possibly by embedding the strip or rod in the flexible polymeric material of hose 100.

Figure 12:
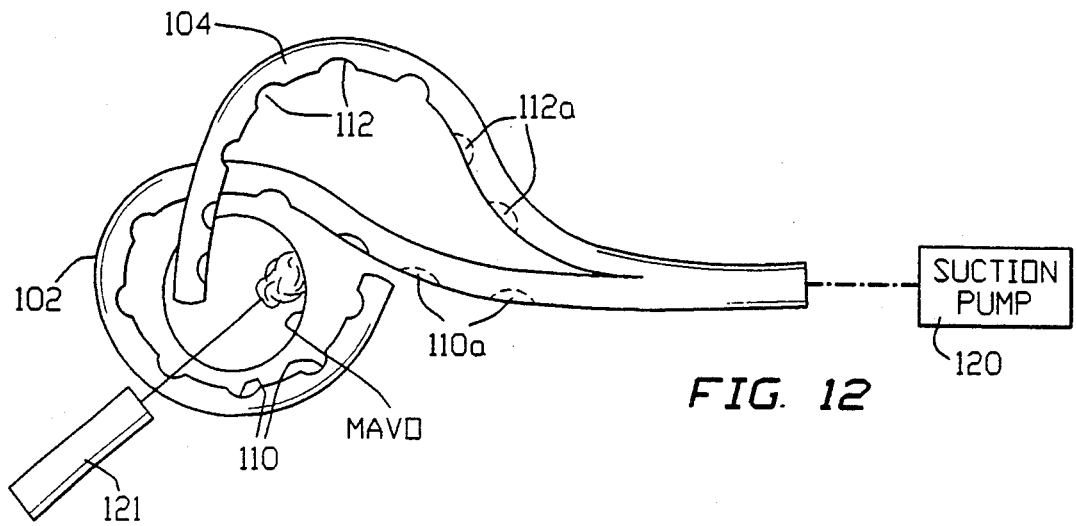
FIG. 12 is a diagrammatic perspective view of the plume evacuator hose of FIG. 11, showing the evacuator hose connected to a vacuum generator and in use during a surgical operation.

As shown in FIG. 12, one prong section 102 of hose 100 can be deformed, by virtue of bendable metal strips 114, to assume a circular or loop-shaped form disposable about a surgical site 118 such as a mouth, anus or vaginal opening MAVO on a patient's skin surface. The other prong section 104 is shaped, by virtue of bendable strip 116, for insertion into the mouth, the rectum or the vagina (or other cavity) cavity. Punch-outs 110a and 110b may be selectively removed to optimize the suction about the surgical site.

Upon connection of hose 100 to a suction pump 120 via coupling 108, an activation of suction pump 120, and a burning or cauterization of diseased skin tissue at the surgical site by a laser device 121, particle-laden air 122 is sucked through opened apertures 110 and 112 into prong sections 102 and 104.

It is to be noted that the punch-outs or covers 13a, 23a, 33a, 110a, 112a which close the plume evacuator suction apertures 13, 23, 33, 110, 112 may be removed via the aid of any convenient surgical tool, such as a clamp or forceps. Even a pen may be used. It is to be further noted that plume evacuator suction apertures 13, 23, 33, 110, 112 may be removably or releasably covered by other, equivalent elements such as tape strips, plugs, frangible membranes, etc.

Figure 13:
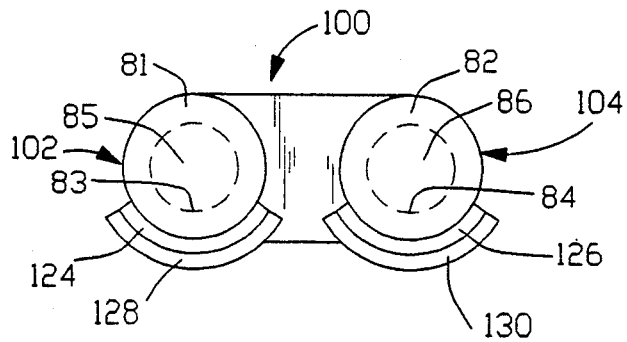
FIG. 13 is a diagrammatic end view of the plume evacuator hose of FIG. 11.

As shown in FIG. 13, prong sections 102 and 104 are provided along lower surfaces with respective two-sided adhesive strips 124 and 126 each covered prior to use of hose 100 by respective release liners 128 and 130. Transverse end walls 81 and 82 at the free ends of prong sections 102 and 104 may be provided with score lines 83 and 84 which define respective circular punch-outs 85 and 86 which may be removed to form circular suction openings.

Figure 14:
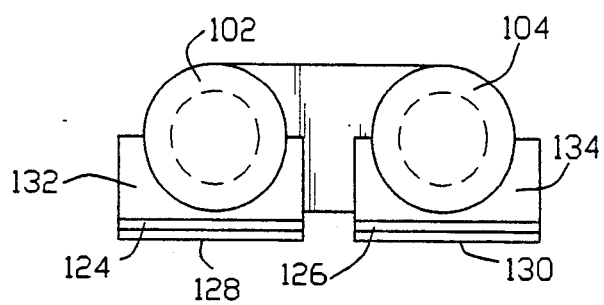
FIG. 14 is a diagrammatic end view of another plume evacuator hose similar to the hose of FIG. 11.

FIG. 14 illustrates that resilient spacer strips 132 and 134 may be provided between adhesive strips 124 and 126, on the one hand, and prong sections 102 and 104, one the other hand, to increase the contact area between the adhesive strips and a skin surface to which prong sections 102 and 104 are to be attached during a surgical procedure.

Figure 15:
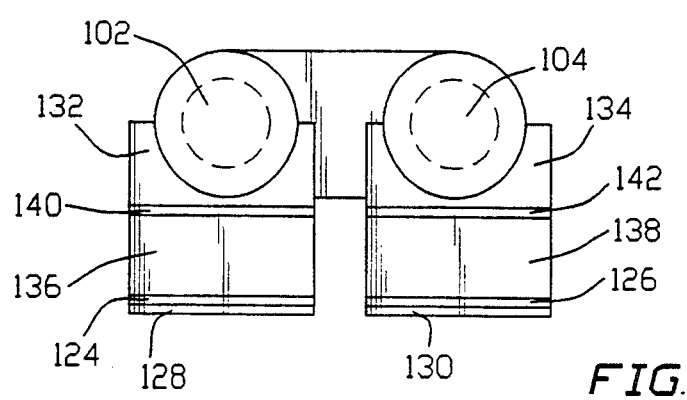
FIG. 15 is a diagrammatic end view of yet another plume evacuator hose similar to the hoses of FIGS. 13 and 14.

As depicted in FIG. 15, further spacer elements 136 and 138 together with respective adhesive layers 140 and 142 may be inserted between two-sided adhesive strips 124 and 126, on the one hand, and spacer strips 132 and 134, on the other hand, to further increase the distance between prong sections 102 and 104 and the patient's skin surface to optimize suction during a surgical procedure.

Although the invention has been described in terms of particular embodiments and applications, one of ordinary skill in the art, in light of this teaching, can generate additional embodiments and modifications without departing from the spirit of or exceeding the scope of the claimed invention. For example, other methods of covering or closing apertures 13, 23, 33, 54, are possible so that they may be easily and selectively opened prior to a surgical operation. One such method involves the placement of a plurality of adhesive strips over respective hose apertures. To open the apertures selected because of their proximity to the surgical site, the respective adhesive strips are peeled away from the hose. Alternatively, a single adhesive strip may cover several suction apertures along the hose. Opening the selected apertures is accomplished by perforating the tape through selected apertures by using an appropriate instrument.

Accordingly, it is to be understood that the drawings and descriptions herein are profferred by way of example to facilitate comprehension of the invention and should not be construed to limit the scope thereof.

What is claimed is:

1. A method for use during surgery, comprising the steps of:
    providing a flexible hose having a plurality of apertures spaced from each other along a linear distal end portion of said hose;
    forming a proximal part of said distal end portion into an arcuate segment about an opening in a patient, said arcuate segment including some of said apertures;
    attaching at least a section of said arcuate segment about the opening;
    inserting a distal end segment of said distal end portion through said opening into a body cavity of the patient, said distal end segment also including some of said apertures;
    connecting a proximal end of said hose to a suction source;
    cauterizing organic tissues in said body cavity;
    generating air-borne particulate matter as a by-product of said step of cauterizing; and
    during said stp of cauterizing, applying suction to said hose to draw in air through the apertures in said arcuate segment and in said distal end segment.

2. The method defined in claim 1 wherein said hose is provided with form retention means attached to said hose for maintaining at least a portion of said hose in a selected substantially loop-shaped configuration, further comprising the step of using said form retention means to maintain said arcuate segment in an arcuate configuration.

3. The device defined in claim 2 wherein said form retention means includes a bendable memory strip, said step of using including the step of bending said memory strip into a desired shape.

4. The method defined in claim 2 wherein said form retention means includes an adhesive strip extending along a length of said hose, said step of using including the step of pressing said adhesive strip to a skin surface about said opening.

5. The method defined in claim 1 wherein said opening is a natural body opening.

6. The method defined in claim 5 wherein said opening is the mouth.

7. The method defined in claim 5 wherein said opening is the anus.

8. The method defined in claim 5 wherein said opening is the vagina.

9. A method for use during laser surgery, comprising the steps of:
    providing a flexible hose having a plurality of apertures spaced from each other along a distal end portion of said hose;
    forming a portion of said hose into an arcuate segment about an opening in a patient, said arcuate segment including some of said apertures;
    attaching at least a section of said arcuate segment about the opening;
    inserting a distal end segment of said hose through said opening into a body cavity of the patient, said distal end segment also including some of said apertures;
    connecting a proximal end of said hose to a suction source;
    applying suction to said hose to draw in air through the apertures in said arcuate segment and in said distal end segment, said hose being provided with cover means attached to said hose for removably covering at least some of said apertures, further comprising the step of removing said cover means to expose apertures along said arcuate segment and said distal end segment prior to said step of applying suction.

10. A method for use during laser surgery, comprising the steps of:
- providing a flexible hose having a plurality of apertures spaced from each other along a distal end portion of said hose;
- forming a portion of said hose into an arcuate segment about an opening in a patient, said arcuate segment including some of said apertures;
- attaching at least a section of said arcuate segment about the opening;
- inserting a distal end segment of said hose through said opening into a body cavity of the patient, said distal end segment also including some of said apertures;
- connecting a proximal end of said hose to a suction source; and
- applying suction to said hose to draw in air through the apertures in said arcuate segment and in said distal end segment, said apertures having diameters and intra-aperture spacings which vary from aperture to aperture, said step of applying suction thus including the step of equalizing suction through said apertures during use of the method.

11. The method defined in claim 1, further comprising the step of disposing said arcuate segment on a spacer element to control the distance of said arcuate segment from said opening.

12. A method for use during laser surgery, comprising the steps of:
- providing a flexible hose bifurcated along a distal end segment into two substantially equivalent hose sections each having a plurality of apertures spaced from each other along the respective hose section;
- forming one of said hose sections into an arcuate segment about an opening in a patient;
- attaching at least a portion of said arcuate segment about the opening;
- inserting the other of said hose sections through said opening into a body cavity of the patient;
- connecting a proximal end of said hose to a suction source; and
- applying suction to said hose to draw in air through the apertures in said arcuate segment and in said other of said hose sections.

* * * * *